US00PP25158P3

(12) United States Plant Patent
Schoone

(10) Patent No.: US PP25,158 P3
(45) Date of Patent: Dec. 9, 2014

(54) ***PHALAENOPSIS* ORCHID PLANT NAMED 'TELLURIDE'**

(50) Latin Name: ***Phalaenopsis* hybrid**
Varietal Denomination: Telluride

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 13 days.

(21) Appl. No.: 13/986,268

(22) Filed: Apr. 18, 2013

(65) Prior Publication Data

US 2013/0291241 P1 Oct. 31, 2013

Related U.S. Application Data

(60) Provisional application No. 61/638,277, filed on Apr. 25, 2012.

(30) Foreign Application Priority Data

Apr. 26, 2012 (NL) ..... OPS895

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Telluride' particularly characterized by flowers which are white with a little yellow in the labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'TELLURIDE'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Telluride'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Telluride' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Telluride' originated from a cross made by the inventor in 1999 in Strengweg, Heemskerk, The Netherlands. The female or seed parent is the *Phalaenopsis* cultivar designated 'Hohoemi×Joseph Hampton×Taisuco Kaaladian', unpatented. The male or pollen parent is the *Phalaenopsis* cultivar designated 'Malibu Real×amabilis', unpatented. The new *Phalaenopsis* 'Telluride' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Telluride', which in combination distinguish this *Phalaenopsis* as a new and distinct cultivar:

1. flowers which are white with a little yellow in the labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Telluride', the flowers of the female parent 'Hohoemi×Joseph Hampton×Taisuco Kaaladian' are about 11 cm high and the flowers of the male parent 'Malibu Real×amabilis' are about 7 cm high, whereas the flowers of 'Telluride' are about 9 cm high.

Presently, there is no other commercial cultivar to which 'Telluride' can be meaningfully compared.

BRIEF DESCRIPTION OF THE PHOTOGRAPHS

The accompanying photographs illustrate the overall appearance of the new *Phalaenopsis* 'Telluride' showing the colors as true as is reasonably possible with colored reproductions of this type. Colors in the photographs may differ slightly from the color values cited in the detailed botanical description, which accurately describe the color of 'Telluride'.

DETAILED BOTANICAL DESCRIPTION

Figure 1:
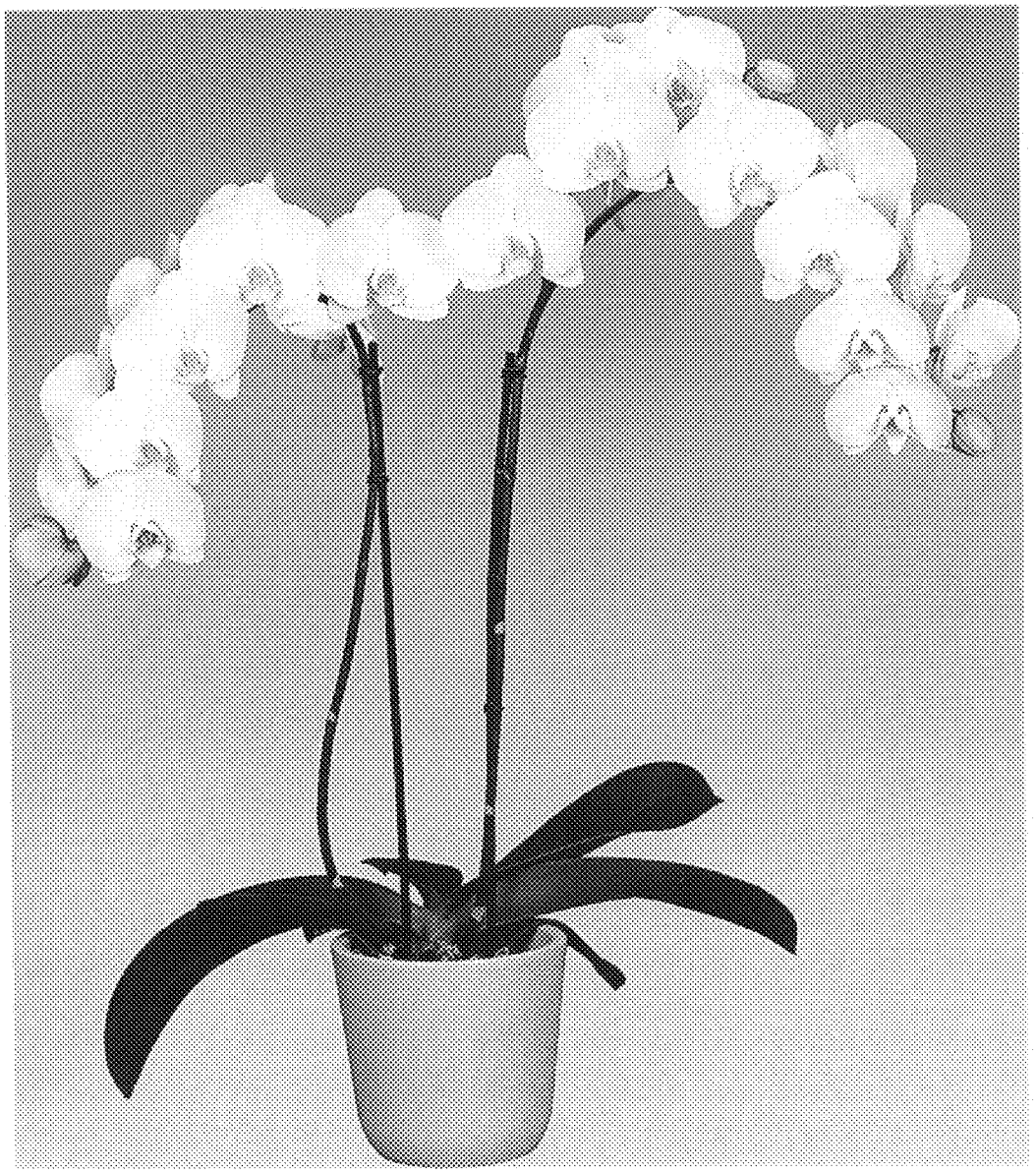
FIG. 1 shows a side view perspective of a typical flowering plant of 'Telluride' in a 12 cm pot, at 16 months of age.

The new *Phalaenopsis* cultivar 'Telluride' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Telluride' as grown in a greenhouse in Strengweg, Heemskerk, The Netherlands, under conditions which closely approximate those generally used in commercial practice. Initially, the ideal temperature to grow plants of 'Telluride' is 27° C. during the day and at night. Then, during the flowering phase of 'Telluride', the ideal growing temperature is 20-22° C. during the day and 18° C. at night. Light levels for growing 'Telluride' are a minimum of 5,000 lux and a maximum of 10,000 lux. A balanced fertilizer with level of 200 ppm N, 87 ppm P, 168 ppm K is applied. Duration of growth of 'Telluride' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Telluride' plants described is 12 months after potting.

Classification:

*Botanical.*—*Phalaenopsis* hybrid.

Parentage:

*Female or seed parent.*—*Phalaenopsis* cultivar designated 'Hohoemi×Joseph Hampton×Taisuco Kaaladian', unpatented.

*Male or pollen parent.*—*Phalaenopsis* cultivar designated 'Malibu Real×amabilis', unpatented.

Propagation:

*Type.*—Tissue culture.

*Rooting habit and description.*—Fleshy; approximately 3 mm-7 mm wide and yellow green in color (RHS 144A and RHS 189C); freely branching. It takes 12 weeks for plants growing in tissue culture to initiate roots.

Plant:

*Size at maturity.*—Height: about 61 cm. Spread: about 65 cm.

*Growth habit.*—Standard; dark green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is little pointy, straight smooth edges and asymmetric.

*Texture* (*upper & underside*).—Smooth and leathery.

*Mature leaf length.*—About 17 to 31 cm.

*Mature leaf width.*—About 6 to 9 mm.

*Mature leaf thickness.*—About 2 mm.

*Mature leaf color.*—Upper side: green (RHS N137B). Under side: green (RHS 138A) with dark edges (N137B).

*Leaf base.*—Acute.

*Margin.*—Entire.

*Venation.*—Pattern: parallel. Color of midvein: upper side: green (RHS N137A). under side: green (RHS 138B).

Raceme:

*Quantity per plant.*—About 1 to 2.

*Number of flowers per raceme.*—About 10.

*Length.*—About 51 to 60 cm.

*Diameter.*—About 5 to 7 mm.

*Strength.*—Strong.

*Aspect.*—Upright.

*Texture.*—Glabrous and smooth.

*Color.*—Yellow-green (RHS 144A).

*Internode.*—Length: about 35 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 25 mm. Diameter (at midpoint): about 25 mm. Shape: egg-shaped/oval. Color: yellow green (RHS 145B).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
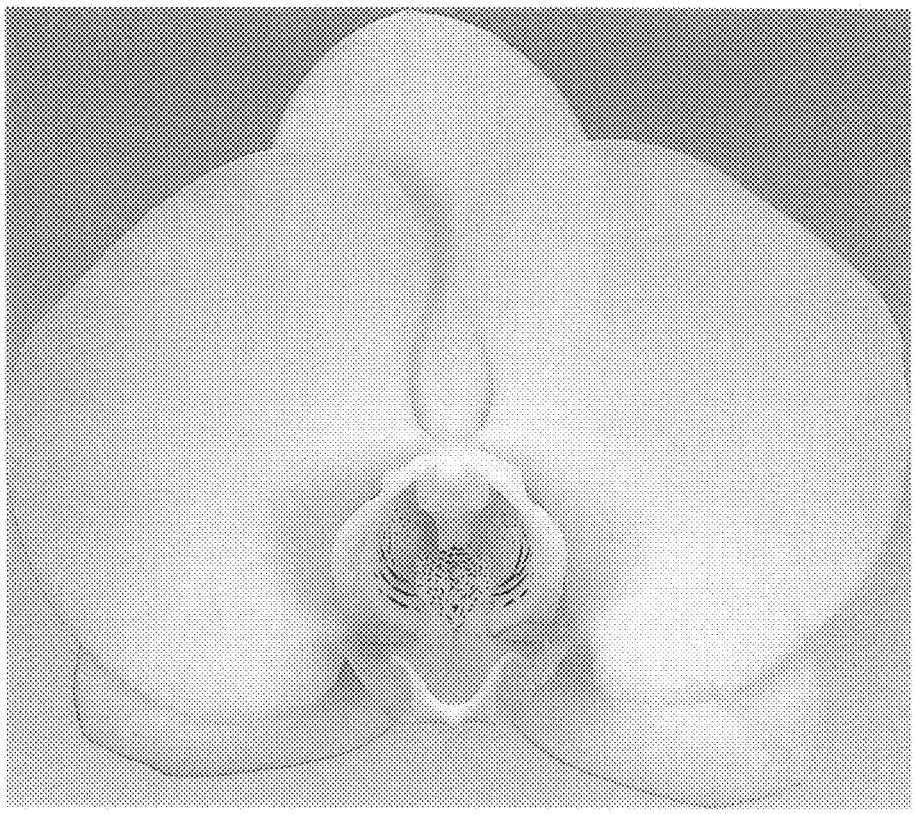
FIG. 2 shows a close-up view of the typical buds and flowers of 'Telluride'.
Figure 3:
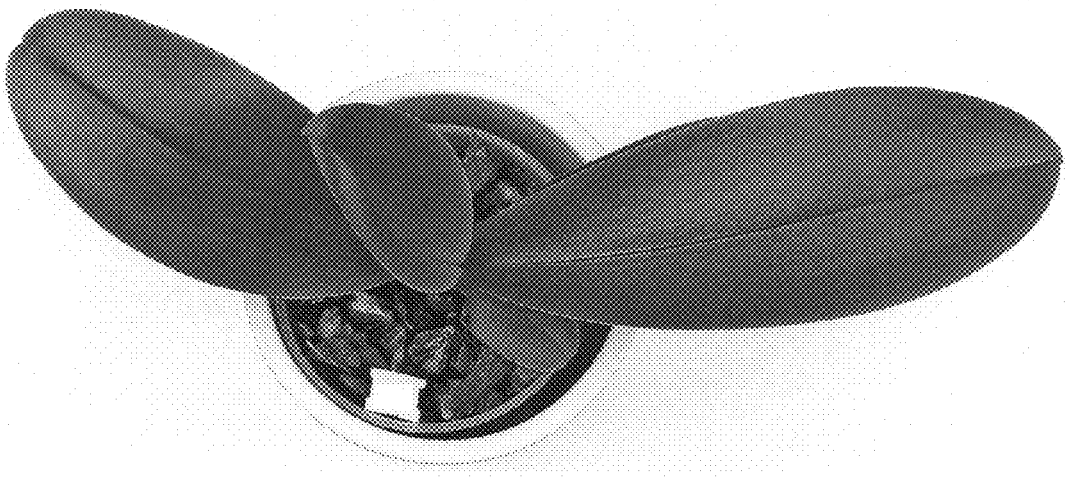
FIG. 3 shows a close-up view of the typical leaves of 'Telluride'.

*Flower*.—Rate of opening: Flowers fully opened about 2 to 3 days after petal and sepal separation. Orientation at opening: slanted upward and outward. Shape: see FIG. 2. Size: Height: about 90 mm. Diameter: about 89 mm. Depth of tube: about 17 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: broadly ovate/round. Margin: entire and weakly undulate. Base: broadly ovate. Length: about 55 mm. Width: about 45 mm. Texture: Upper surface: smooth and satiny. Under surface: smooth and satiny. Color (when fully opened): upper side: edges are white (RHS NN155C). Under side: edges are white (RHS NN155C).

*Labellum*.—Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the mid lobe is triangular with a bump and a rib on it. Margin: entire. Apex: oval. Length: about 21 mm. Width (not flattened): about 22 mm. Texture: Upper and under surface: smooth and satiny. Color (when fully opened): Mid lobe: upper surface: Main color white (RHS NN155C). Green/yellow (RHS 1A) at the base left and right and a line in the center. At the base also a purple haze (RHS N80B) and some red/purple spots (RHS 59C). At the edge a small stripe grey/orange (RHS 163A). Under surface: main color is white (RHS NN155C) at the base left and right some green/yellow (RHS 1A) and at the edge grey/orange (RHS 163A). At the base also a purple/violet haze (RHS N81D). Lateral lobes: upper surface: Main color is white (RHS NN155C), edge yellow (RHS 5A) and some green (RHS150B). At the base red/purple stripes (RHS 59C). Under surface: white (RHS NN155C) edge yellow (RHS 5A) and some green (RHS 150B). At the base some purple/violet spots (RHS N81D). Chirri: long, little curly (about 19 mm). color: yellow (RHS 5A). Pestle (Callosities): Length: about 7 mm. Width (not flattened): about 5 mm. Color: main color is white (RHS NN155C) with yellow edges and yellow inside (RHS 5A) and red/purple spots (RHS 59C).

*Sepals*.—Arrangement: Outer whorl comprises 3 sepals. Overall shape: egg-shaped (runs out into a point) and weakly cupped. Margin: entire and weakly undulate. Length: about 46 mm. Width: about 33 mm. Apex: blunt top with a small point. Texture: Upper and under surface: smooth and satiny. Color (when fully opened): upper side: Main color is white (RHS NN155C). At lateral sepals at the base a vague yellow/green mark (RHS 146D) with red/purple spots (RHS59C). Under side: main color is white (RHS NN155C). At the base a yellow/green haze (RHS145C) and a purple/red haze (RHS N74B). This purple/red haze is clearer at the lateral sepals as with the dorsal sepal. Some also have a little purple/red (RHS 74B) on the midvein.

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 9 mm. Diameter: about 6 mm. Color: white (RHS NN155C). Pollinia: Quantity: two. Diameter: about 1 mm. Color: yellow-orange (RHS 23A).

*Ovary*.—Length: about 3 mm. Diameter: about 5 mm. Color: white (RHS NN155C).

*Pedicel*.—Length: about 35 mm. Diameter: about 2 mm to 4 mm. Texture: glabrous and smooth. Color: yellow/green (RHS 146A) to yellow/green (RHS 145C) and close to the flower a haze (RHS N80B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Telluride', as illustrated and described herein.

* * * * *